United States Patent [19]

Koulbanis et al.

[11] 4,437,895

[45] Mar. 20, 1984

[54] MIXTURE OF VEGETABLE OILS BASED ON JOJOBA OIL AND COSMETIC COMPOSITIONS COMPRISING THE MIXTURE

[75] Inventors: Constantin Koulbanis, Paris; Quang L. N'Guyen, Antony; Arlette Zabotto, Paris; Josiane Plot, Aulnay-sous-Bois, all of France

[73] Assignee: Societe Anonyme dite: L'Oreal, Paris, France

[21] Appl. No.: 400,221

[22] Filed: Jul. 20, 1982

[30] Foreign Application Priority Data

Jul. 23, 1981 [FR] France ................................ 8114366

[51] Int. Cl.³ ................... C08L 91/00; C09D 3/26; A61K 7/48
[52] U.S. Cl. ................................. 106/245; 106/250; 106/251
[58] Field of Search ............... 106/243, 253, 270, 268, 106/245, 250; 424/312, 195, 365

[56] References Cited

U.S. PATENT DOCUMENTS

| 4,324,802 | 4/1982 | Koulbanis | 424/60 |
| 4,329,298 | 5/1982 | Brown et al. | 106/243 |
| 4,360,387 | 11/1982 | Borwn et al. | 106/243 |

FOREIGN PATENT DOCUMENTS

| 2474310 | 7/1981 | France . |
| 2479688 | 10/1981 | France . |
| 2066071 | 7/1981 | United Kingdom . |

OTHER PUBLICATIONS

Chem. Abstract 83: 103164z Watanabe, May 75.
Chem. Abstracts, vol. 89, No. 11, p. 408 No. 89126d.

*Primary Examiner*—Theodore Morris
*Attorney, Agent, or Firm*—Cushman, Darby & Cushman

[57] ABSTRACT

A mixture of vegetable oils is disclosed which is stable to oxidation, contains at least 5% of jojoba oil, the remainder consisting essentially of at least one other vegetable oil which is hazelnut oil, mango oil, coffee bean wax, karite butter, soya oil, palm oil or maize germ oil.

10 Claims, No Drawings

MIXTURE OF VEGETABLE OILS BASED ON JOJOBA OIL AND COSMETIC COMPOSITIONS COMPRISING THE MIXTURE

This invention relates, on the one hand, to a mixture of vegetable oils based on jojoba oil, the latter acting as a stabiliser towards oxidation by atmospheric oxygen, and, on the other hand, to various cosmetic compositions in which such a mixture is present.

For the cosmetician, oils constitute an important class of substances forming part of the majority of cosmetic compositions and especially of emulsions, whether these be of the oil-in-water or water-in-oil type.

These oils, called "cosmetic oils", are greasy products which are liquid or slightly pasty at ambient temperature.

They can be of very varied origin and can be, in particular, vegetable or animal oils, mineral oils or, alternatively, synthetic oils.

Vegetable oils constitute a particularly important class, but their use has very frequently been limited insofar as they lack stability, thus leading to the phenomenon of growing rancid, caused by their oxidation by atmospheric oxygen.

The vast majority of vegetable oils in fact contain a relatively high percentage of unsaturated products which are very sensitive to oxidation, so that cosmeticians tend to replace vegetable oils by mineral oils or synthetic oils, but the latter do not always make it possible to impart the desired properties to the compositions.

As the current tendency is orientated more particularly towards the use of natural products, attempts have been made in particular to stabilise vegetable oils with the aid of antioxidants, but excellent results have not been observed.

Research has therefore been directed towards particular mixtures of vegetable oils, and it has been found, surprisingly, according to the present invention, that certain vegetable oils can be stabilised if they contain a certain percentage of jojoba oil.

In fact, numerous experiments we have carried out have made it possible to show that jojoba oil is capable of exerting a noteworthy stabilising action on certain vegetable oils and waxes which are particularly sensitive to oxidation.

The present invention accordingly provides a mixture of vegetable oils, which is stable to oxidation and which contains at least 5% of jojoba oil, the remainder consisting essentially of at least one other vegetable oil or wax taken from the group comprising hazelnut oil, mango oil, coffee bean wax, karite butter, soya oil, palm oil and maize germ oil.

Jojoba oil is a vegetable oil which is liquid at ambient temperature; it can be extracted from *Simmondsia chinensis*, and has the following characteristics:
Viscosity: (Brookfield, 25° C.) about 37 cp.
Colour: Light yellow to colourless (refined).
Density at 25° C.: About 0.863.
Iodine number: 80-82.
$n_D^{25°\,C.} = 1.4645$-$1.4650$.

According to the invention, the jojoba oil is preferably present in an amount of at least 5% and more particularly of 10 to 95% by weight, relative to the total weight of the mixture. All percentages throughout this specification are by weight, unless otherwise stated.

Despite numerous studies carried out on this particular property of jojoba oil, it has not been possible, at least for the moment, to determine the reasons for which this activity is essentially limited to certain vegetable oils. In fact, with vegetable oils other than those listed above, it has not been possible to observe a significant stabilising action exerted by jojoba oil, even at relatively high concentrations.

Typical characteristics of the oils which can be stabilised by jojoba oil, according to the present invention are as follows:

Hazelnut Oil
colour: light yellow.
density at 15° C.: 0.914 to 0.920.
iodine number: 83 to 90.
$n_D^{20°\,C.} = 1.4690$.

Mango Oil
colour: white-pale yellow.
iodine number: 30 to 55.

Coffee Bean Wax
melting point: 49° C.

Karite Butter
colour: white-pale yellow.
density at 20° C.: 0.940.
iodine number: 40 to 70.
$n_D^{49°\,C.} = 1.46333$ to $1.4668$.

Soya Oil
colour: yellow-pale yellow.
density at 15° C.: 0.924 to 0.927.
iodine number: 103 to 152.
$n_D^{20°\,C.} = 1.4720$ to $1.4766$.

Palm Oil (Distilled)
density at 15° C.: 0.92 to 0.945.
iodine number: 48 to 52.
$n_D^{60°\,C.} = 1.445$ to $1.452$.

Maize Germ Oil
colour: yellow.
density at 15° C.: 0.916 to 0.921.
iodine number: 109 to 133.
$n_D^{15°\,C.} = 1.4700$ to $1.4740$.

The mixture of vegetable oils according to the invention can be not only a binary mixture, but also a ternary mixture, quaternary or higher mixture, when more than one vegetable oil such as those listed above are associated with jojoba oil.

Amongst the binary mixtures which have led to the most significant results, the following mixtures may be listed in particular:
jojoba oil 30 to 95%/hazelnut oil 70 to 5%
jojoba oil 5 to 50%/mango oil 95 to 50%
jojoba oil 5 to 95%/coffee bean wax 95 to 5%
jojoba oil 20 to 80%/karite butter 80 to 20%
jojoba oil 5 to 60%/soya oil 95 to 40%
jojoba oil 5 to 95%/palm oil 95 to 5%
jojoba oil 15 to 85%/maize germ oil 85 to 15%

It must be pointed out that, despite their consistency, coffee bean wax and also karite butter are generally considered as cosmetic oils.

The present invention also provides cosmetic compositions containing the mixture of vegetable oils which is stable to oxidation, as defined above.

These cosmetic compositions are, in general, all compositions containing oils. Amongst these compositions, there may be mentioned, in particular, those which are presented in the form of fluid emulsions (milks), or lotions, or in the form of emulsions of thicker consistency (creams).

Examples of these compositions are milks or emollient creams, milks or creams for the hands, make-up removal creams or milks, make-up foundation bases, "antisunburn" milks or creams, milks or creams for artificial tanning, anti-perspirant milks or creams and shaving creams or foams.

These cosmetic compositions can also be presented in the form of sticks or the lips, intended either for colouring them or for preventing cracking, or in the form of make-up products for the eyes or rouges.

According to the invention, the mixture of vegetable oils which is stable to oxidation represents from 5 to 99% by weight, relative to the total weight of the cosmetic composition.

According to one embodiment, the cosmetic composition consists essentially of the mixture of vegetable oils, in which case it is in the form of, for example, an anti-sunburn oil (containing a sun filter absorbing ultraviolet), an oil for the hands, an oil for the body, a pre-shave or after-shave oil or oil for the bath.

The compositions according to the invention generally contain other ingredients, in particular preservatives, perfumes or colorants.

Because of the stabilising action of the jojoba oil, the use of an antioxidant is not generally necessary.

If the compositions according to the invention are present in the form of emulsions of the water-in-oil or oil-in-water type, the oil phase can consist essentially of the mixture of vegetable oils according to the invention, if desired together with at least one other oil which does not grow rancid, preferably a synthetic oil, and/or at least one wax.

The oil phase of the emulsions is suitably from 5 to 60% by weight, relaive to the total weight of the emulsion.

The water phase of the said emulsions is preferably 30 to 85%, relative to the total weight of the emulsion.

The amount of the emulsifier is generally 1 to 20% and preferably 2 to 12%.

The emulsions according to the invention can also contain so-called filler substances, such as titanium oxide, zinc oxide, talc or kaolin, and also colouring substances, in particular iron oxides, such as red iron oxide, yellow iron oxide and black iron oxide.

The following Examples further illustrate the present invention.

EXAMPLE 1

A face cream is prepared according to the invention by mixing the following ingredients:

| | |
|---|---|
| Self-emulsifiable glycerol monostearate | 5% |
| Stearic acid | 5% |
| Cetyl alcohol | 0.5% |
| Triethanolamine | 1.4% |
| Mixture of vegetable oils: | |
| Jojoba oil 75% | } 24% |
| Palm oil (distilled) 25% | |
| Carboxyvinyl polymer (Carbopol 940) | 0.4% |
| Water (+ perfume and preservative) q.s. | 100% |

EXAMPLE 2

A body milk is prepared according to the invention by mixing the following ingredients:

| | |
|---|---|
| Stearic acid | 1.4% |
| Self-emulsifiable glycerol monostearate | 2% |
| Cetyl alcohol | 0.5% |
| Mixture of vegetable oils: | |
| Jojoba oil 70% | } 20% |
| Maize germ oil 30% | |
| Carboxyvinyl polymer | 0.25% |
| Triethanolamine | 1.25% |
| Propylene glycol | 3% |
| Water (+ perfume and preservative) q.s. | 100% |

EXAMPLE 3

A night cream is prepared according to the invention by mixing the following ingredients:

| | |
|---|---|
| Mg lanolate | 2.85% |
| Lanolin alcohol | 6.65% |
| Ozokerite | 2% |
| Mixture of vegetable oils: | |
| Jojoba oil 40% | } 30% |
| Hazelnut oil 60% | |
| Water (+ perfume and preservative) q.s. | 100% |

EXAMPLE 4

A face oil is prepared by mixing the following ingredients:

| | |
|---|---|
| Mixture of vegetable oils: | |
| Jojoba oil 56% | } 98.5% |
| Soya oil 44% | |
| Vitamin A palmitate | 1% |
| Perfume | 0.5% |

EXAMPLES 5 to 7

White substances for the preparation of make-up products are prepared according to the invention by mixing the following ingredients:

EXAMPLE 5

| | |
|---|---|
| Microcrystalline wax | 13% |
| 1-Docosanoyl-3-(2-ethylhexyloxy)-propan-2-ol | 13% |
| Vinyl acetate 35%/alkyl stearate 65% polymer | 10% |
| Liquid lanolin | 12% |
| Triglycerides of $C_8$–$C_{12}$ saturated fatty acids of the vegetable origin | 8.5% |
| Arachidyl propionate | 5% |
| Vegetol calendula oil | 8% |
| Glycol distearate | 3.5% |
| Modified lanolin | 8% |
| Acetoglyceride LC | 4% |
| Mixture of vegetable oils: | |
| Jojoba oil 80% | } 15% |
| Karite butter 20% | |

EXAMPLE 6

| | |
|---|---|
| Microcrystalline wax | 13% |
| 1-Docosanoyl-3-(2-ethylhexyloxy)-propan-2-ol | 13% |
| Vinyl acetate 35%/alkyl stearate 65% polymer | 10% |
| Liquid lanolin | 12% |
| Triglycerides of C$_8$–C$_{12}$ saturated fatty acids of vegetable origin | 8.5% |
| Arachidyl propionate | 5% |
| Vegetol calendula oil | 8% |
| Glycol distearate | 3.5% |
| Modified lanolin | 8% |
| Acetoglyceride LC | 4% |
| Mixture of vegetable oils: | |
| Jojoba oil 70% | } 15% |
| Coffee bean wax 30% | |

EXAMPLE 7

| | |
|---|---|
| Microcrystalline wax | 13% |
| 1-Docosanoyl-3-(2-ethylhexyloxy)-propan-2-ol | 13% |
| Vinyl acetate 35%/alkyl stearate 65% polymer | 10% |
| Liquid lanolin | 12% |
| Triglycerides of C$_8$–C$_{12}$ saturated fatty acids of vegetable origin | 8.5% |
| Arachidyl propionate | 5% |
| Vegetol calendula oil | 8% |
| Glycol distearate | 3.5% |
| Modified lanolin | 8% |
| Acetoglyceride LC | 4% |
| Mixture of vegetable oils: | |
| Jojoba oil 50% | } 15% |
| Mango oil 50% | |

EXAMPLES 8 to 10

Lipsticks are prepared according to the invention by mixing the following ingredients:

EXAMPLE 8

| | |
|---|---|
| White substance according to Example 5 | 90% |
| Titanium oxide (rutile) | 2% |
| DC RED 7, Ca salt, on colophony | 2% |
| Red iron oxide | 2% |
| DC RED 21, Al lake, on alumina | 2% |
| DC RED 36 | 1% |
| Perfume | 1% |

EXAMPLE 9

| | |
|---|---|
| White substance according to Example 6 | 85% |
| DC RED 8, Na salt | 2% |
| DC RED 7, Ca salt, on colophony | 2% |
| Titanium mica | 10% |
| Perfume | 1% |

EXAMPLE 10

| | |
|---|---|
| White substance according to Example 7 | 92% |
| Red iron oxide | 1% |
| Yellow iron oxide | 1% |
| DC RED 7, Ca salt, on colophony | 2% |
| DC YELLOW 6, Al salt, on alumina | 2% |
| DC RED 36 | 1.5% |
| Perfume | 0.5% |

EXAMPLE 11

A rouge in the form of an oil-in-water emulsion is prepared according to the invention by mixing the following ingredients:

| | |
|---|---|
| Stearic acid | 2% |
| Polyoxyethyleneated sorbitan monostearate | 0.5% |
| Mixture of vegetable oils: | |
| Jojoba oil 50% | } 20% |
| Mango oil 50% | |
| Triethanolamine | 1% |
| Glycerol | 5% |
| Propylene glycol | 5% |
| Hydroxyethylcellulose | 1.5% |
| Silicates with a high Mg content | 2% |
| Titanium dioxide | 1% |
| Iron oxides | 2% |
| Titanium mica | 5% |
| D and C Red 7, calcium lake, on colophony | 0.3% |
| Softened water q.s. | 100% |

EXAMPLE 12

A make-up foundation is prepared according to the invention by mixing the following ingredients:

| | |
|---|---|
| Stearic acid | 2% |
| Glycerol monostearate and distearate | 2% |
| Triglycerides of saturated fatty acids of vegetable origin | 3% |
| Mixture of vegetable oils: | |
| Jojoba oil 44.5% | } 9% |
| Karite butter 55.5% | |
| Perhydrosqualene | 5% |
| Hydrogenated polyisobutene | 8% |
| Propyl para-hydroxybenzoate | 0.10% |
| Cyclic methylpolysiloxane | 5% |
| Methyl para-hydroxybenzoate | 0.10% |
| Propylene glycol | 5% |
| Yellow iron oxide | 0.82% |
| Red iron oxide | 0.55% |
| Black iron oxide | 0.13% |
| Titanium dioxide | 6.50% |
| Magnesium aluminium silicate | 0.80% |
| Sodium carboxymethylcellulose | 0.16% |
| Triethanolamine | 0.90% |
| Imidazolidinylurea | 0.30% |
| Scenting composition | 0.30% |
| Sterile softened water q.s. | 100% |

We claim:

1. An oxidation stable mixture comprising 5–95 percent by weight of jojoba oil, the remainder being a member selected from the group consisting of hazelnut oil, mango oil, coffee bean wax, karite butter, soya oil, palm oil, maize germ oil and mixtures thereof.

2. An oxidation stable mixture comprising from 30 to 95 weight percent jojoba oil and from 70 to 5 weight percent hazelnut oil.

3. An oxidation stable mixture comprising from 5 to 50 weight percent jojoba oil and from 95 to 50 weight percent mango oil.

4. An oxidaton stable mixture comprising 5 to 95 weight percent jojoba oil and from 95 to 5 weight percent coffee bean wax.

5. An oxidation stable mixture comprising from 20 to 80 weight percent jojoba oil and from 80 to 20 weight percent karite butter.

6. A composition suitble for use in cosmetics comprising from 5 to 99 weight percent, relative to the total weight of said composition, of an oxidation stable mixture comprising jojoba oil in an amount of 5 to 95 percent by weight of said mixture, the remainder of said mixture being a member selected from the group consisting of hazelnut oil, mango oil, coffee bean wax, karite butter, soya oil, palm oil, maize germ oil and mixtures thereof.

7. A mixture according to claim 1, which comprises from 5 to 60% by weight of jojoba oil and from 95 to 40% by weight of soya oil.

8. A mixture according to claim 1, which comprises from 5 to 95% by weight of jojoba oil and from 95 to 5% by weight of palm oil.

9. A mixture according to claim 1, which comprises from 15 to 85% by weight of jojoba oil and from 85 to 15% by weight of maize germ oil.

10. A water-in-oil or oil-in-water emulsion wherein the oil phase represents from 5 to 60 weight percent of the total weight of said emulsion, said oil phase being an oxidation stable mixture comprising 5-95 percent by weight of jojoba oil, the remainder of said mixture being a member selected from the group consisting of hazelnut oil, mango oil, coffee bean wax, karite butter, soya oil, palm oil, maize germ oil and mixtures thereof.

* * * * *